(12) United States Patent
Yudina et al.

(10) Patent No.: US 10,857,090 B2
(45) Date of Patent: Dec. 8, 2020

(54) ORAL COMPOSITIONS

(71) Applicant: Stellar Biome Inc., London (CA)

(72) Inventors: Natalia Yudina, London (CA); Maxim Daniel Seferovic, London (CA)

(73) Assignee: Stellar Biome Inc., London (CA)

( * ) Notice: Subject to any disclaimer, the term of this patent is extended or adjusted under 35 U.S.C. 154(b) by 15 days.

(21) Appl. No.: 14/902,714

(22) PCT Filed: Jul. 4, 2014

(86) PCT No.: PCT/CA2014/050642
§ 371 (c)(1),
(2) Date: Jan. 4, 2016

(87) PCT Pub. No.: WO2015/000082
PCT Pub. Date: Jan. 8, 2015

(65) Prior Publication Data
US 2016/0166501 A1    Jun. 16, 2016

Related U.S. Application Data

(60) Provisional application No. 61/843,158, filed on Jul. 5, 2013.

(51) Int. Cl.
*A61K 8/99* (2017.01)
*A61Q 11/00* (2006.01)
*A61K 35/747* (2015.01)
*A61K 8/64* (2006.01)

(52) U.S. Cl.
CPC .................. *A61K 8/99* (2013.01); *A61K 8/64* (2013.01); *A61K 35/747* (2013.01); *A61Q 11/00* (2013.01); *A61K 2800/5922* (2013.01)

(58) Field of Classification Search
CPC .......... A61K 2800/5922; A61K 35/747; A61K 8/64; A61K 8/99; A61Q 11/00; A23Y 2220/39
See application file for complete search history.

(56) References Cited

U.S. PATENT DOCUMENTS

| | | | |
|---|---|---|---|
| 4,425,468 A | 1/1984 | Makhlouf et al. | |
| 4,569,966 A | 2/1986 | Piccirilli et al. | |
| 8,288,485 B2 | 10/2012 | Koch et al. | |
| 9,155,766 B2 | 10/2015 | Ioudina | |
| 2002/0012637 A1* | 1/2002 | Neeser .................... | A61P 43/00 424/50 |
| 2010/0310513 A1* | 12/2010 | Daube .................. | A23C 9/1234 424/93.2 |
| 2012/0207712 A1 | 8/2012 | Longoni et al. | |
| 2016/0037811 A1 | 2/2016 | Xiao et al. | |

FOREIGN PATENT DOCUMENTS

| | | |
|---|---|---|
| CN | 103190626 A | 7/2013 |
| DE | 3248132 A1 | 7/1983 |
| DE | 3513248 A1 | 11/1985 |
| DE | 102005035235 A1 | 2/2007 |
| EP | 0318939 A2 | 6/1989 |
| EP | 0320690 A2 | 6/1989 |
| EP | 0699689 B1 | 12/1999 |
| EP | 1104281 A1 | 6/2001 |
| EP | 2169677 A1 | 3/2010 |
| EP | 2420580 | 2/2012 |
| JP | 2003-502375 | 1/2003 |
| JP | 2008-517015 | 5/2008 |
| JP | 5328158 | 10/2013 |
| WO | WO-00/78322 | 12/2000 |
| WO | WO 01/15715 | * 3/2001 |
| WO | WO-01/15715 | 3/2001 |
| WO | WO-2006/045474 | 5/2006 |
| WO | WO-2007/086573 | 8/2007 |
| WO | WO-2010/081126 | 7/2010 |
| WO | WO-2011/075549 A1 | 6/2011 |
| WO | WO-2012/005221 A1 | 1/2012 |

OTHER PUBLICATIONS

Chen et al. (2010) Expert Opinion on Therapeutic Patents 20(5): 681-694.*
Philstrom et al. (2005) LOancet 366(9499); 1809-1820 (Year: 2005).*
Wagar et al. (2009) J. Food Sci. Tech. 74(8): M423-M430 (Year: 2009).*
Foster et al. (2011) Beneficial Microbes 2(4): 319-334 (Year: 2011).*
Giglielmetti et al. (2010) Infection and Immunity 78(11): 4734-4743 (Year: 2010).*
Paturi et al. (2007) Int J Food Microbiol 115: 115-118 (Year: 2007).*
Tompkins et al. "Complete Genome Sequence of Lactobacillus helveticus R0052, a Commercial Probiotic Strain" Journal of Bacteriology Nov. 2012 vol. 194 No. 22, p. 6349 (Year: 2012).*
Ong et al. "Influence of Probiotic Lactobacillus acidophilus and L. helveticus on Proteolysis, Organic Acid Profiles, and ACE-Inhibitory Activity of cheddar Cheeses Ripened at 4, 8, and 12 ° C" Journal of Food Science vol. 73, No. 3, 2008 10 pages (Year: 2008).*
Search Report and Written Opinion issued by the Intellectual Property Office of Singapore in related Application No. SG 3577037, issued with Invitation to respond to Written Opinion dated Dec. 13, 2016.
Mintel GNPD, "Oral Care Oven Baked Biscuits for Dogs," published Oct. 2011, [online], [retrieved on Dec. 16, 2016]. Retreived from the Internet: <URL: http://www.gnpd.com/sinatra/recordpage/1652832/from_search/yVHm6pQGci/?page=1>.

(Continued)

*Primary Examiner* — Thane Underdahl
(74) *Attorney, Agent, or Firm* — Arnall Golden Gregory LLP

(57) ABSTRACT

Compositions for use in oral hygiene contain a *Lactobacillus helveticus* strain. Compositions further containing a *Lactobacillus plantarum* strain, especially *Lactobacillus plantarum* SD5870, are particularly effective. The combination of *Lactobacillus helveticus* LAFTI L10 and *Lactobacillus plantarum* SD5870 synergistically improves oral hygiene. The compositions are particularly useful against dental caries.

9 Claims, 8 Drawing Sheets

Specification includes a Sequence Listing.

(56) References Cited

OTHER PUBLICATIONS

Extended European Search Report issued in related application No. EP 14819893.0, dated Jan. 3, 2017.
Burton et al., "Influence of the probiotic Streptococcus salivarius strain M18 on indices of dental health in children: A randomized double-blind, placebo-controlled trial," *J Med Microbiol.* 2013;62(PART6):875-884.
Haukioja, "Probiotics and Oral Health," Eur. J. Dent. Jul. 8, 2010 (Aug. 7, 2010), vol. 4(3), pp. 348-355, ISSN 1305-7464.
International Preliminary Report on Patentability for PCT/CA2014/050642, dated Jan. 5, 2016.
International Search Report and Written Opinion for PCT/CA2014/050642, dated Oct. 14, 2014.
Kang et al., "Inhibitory effect of Lactobacillus reuteri on periodontopathic and cariogenic bacteria," *J Microbiol.* 2011;49(2):193-199.
Keller et al., "Co-aggregation and growth inhibition of probiotic lactobacilli and clinical isolates of mutans streptococci: An in vitro study," *Acta Odontol Scand.* 2011;69(5):263-268.
Näse et al., "Effect of long-term consumption of a probiotic bacterium, Lactobacillus rhamnosus GG, in milk on dental caries and caries risk in children," *Caries Res.* 2001;35(6):412-420.
Oho et al., "Simple and rapid detection of Streptococcus mutans and Streptococcus sobrinus in human saliva by polymerase chain reaction," *Oral Microbiol Immunol.* 2000;15(4):258-262.
Paturi et al., "Effect of Pro biotic Strains Lactobacillus acidophilus LAFTI L10 and Lactobacillus paracasei LAFTI L26 on Systemic Inunune Functions and Bacterial Translocation in Mice," J. Food Prot. Apr. 2008 (Apr. 2008), vol. 71(4), pp. 796-801, ISSN 0362-028X.
Saha et al., "Probiotics as oral health biotherapeutics," *Expert Opin Biol Ther.* 2012;12(9):1207-1220.
Stecksén-Blicks et al., "Effect of long-term consumption of milk supplemented with probiotic lactobacilli and fluoride on dental caries and general health in preschool children: A cluster-randomized study," *Caries Res.* 2009;43(5):374-381.
Tagg et al. ""Fingerprinting" β-haemolytic streptococci by their production of and sensitivity to bacteriocine-like inhibitors," J Med Microbiol., 1979; 12(4):397-411.
Tagg et al., "Bacterial replacement therapy: Adapting "germ warfare" to infection prevention," *Trends Biotechnol.* 2003;21(5):217-223.
Taipale et al., "*Bifidobacterium animalis* subsp. *lactis* BB-12 administration in early childhood: a randomized clinical trial of effects on oral colonization by mutans streptococci and the probiotic," *Caries Res.* 2012;46(1):69-77.
Wang et al., "Synergistic Effects of Nanosecond Pulsed Electric Fields Combined With Low Concentration of Gemcitabine on Human Oral Squamous Cell Carcinoma In Vitro," PLoS One. 2012;7(8):e43213.
Çaglar E et al., "Salivary mutans streptococci and lactobacilli levels after ingestion of the probiotic bacterium Lactobacillus reuteri ATCC 55730 by straws or tablets," *Acta Odontol Scand.* 2006;64(5):314-318.
Çaglar et al., "Bacteriotherapy and probiotics' role on oral health," *Oral Dis.* 2005;11(3):131-137.
Çaglar et al., "Effect of yogurt with Bifidobacterium DN-173 010 on salivary mutans streptococci and lactobacilli in young adults," *Acta Odontol Scand.* 2005;63(6):317-320.
Çaglar et al., "Short-term effect of ice-cream containing *Bifidobacterium lactis* Bb-12 on the number of salivary mutans streptococci and lactobacilli," *Acta Odontol Scand.* 2008;66(3):154-158.
Notification of Reasons for Rejection issued in Japanese Patent Application No. 2016-522158, dated Feb. 23, 2018.
"Periodontitis and Dental Caries Occur Together," Elsevier Journal of Evidence Based Dental Practice, 2012; 12(3), Supplement, pp. 18-19. [online], [retrieved on Sep. 4, 2019]. Retrieved from the Internet: <URL: https://www.sciencedirect.com/science/article/abs/pii/S1532338212700052>. (abstract only).
Aceti et al., "Review: Filling the gaps: current research directions for a rational use of probiotics in preterm infants," Nutrients 2018; 10(1472).
Article "Probiotics", International Scientific Association for Probiotics and Prebiotics, [online], [retrieved on Sep. 4, 2019]. Retrieved from the Internet: <URL: https://isappscience.org/for-scientists/resources/probiotics/>.
De Simone, "The Unregulated Probiotic Market," Clinical Gastroenterology and Hepatology, 2019; 17(5): pp. 809-817.
Guarner et al., "Gut flora in health and disease." Lancet, 2003; 361(9356): pp. 512-519. (abstract only).
Hill et al., "The International Scientific Association for Probiotics and Prebiotics consensus statement on the scope and appropriate use of the term probiotic," Nature Reviews Gastroenterology & Hepatology, 2014; 11: pp. 506-514.
Listerine®, What is Biofilm and Can it Lead to Gum Disease? |Listerine®. [online], [retrieved on Sep. 4, 2019]. Retrieved from the Internet: <URL: https://www.listerine.com/gum-disease-healthy-gums/biofilm>.

* cited by examiner

| | |
|---|---|
| i | Area of probiotic swab |
| ii-vi | Strains of *S. mutans* |
| A | 1 cm |
| B | Area of no growth |
| ZOI | Zone of inhibition = B - A |

| | S. mutans 25175 | | S. mutans 13 | | | S. mutans 14 | | | S. mutans 15 | | | S. mutans 17 | | |
|---|---|---|---|---|---|---|---|---|---|---|---|---|---|---|
| | Ave (mm) | p | SQ | Ave (mm) | p | SQ | Ave (mm) | p | SQ | Ave (mm) | p | SQ | Ave (mm) | p | SQ |
| K12 + M18 | 0.00 | | NA | 1.00 | | 0.08 | 1.00 | | 0.08 | 1.25 | | 1.67 | 0.00 | | NA |
| K12 + LAFTI L10 | 0.00 | | NA | 6.75 | | 0.42 | 6.75 | | 0.10 | 4.50 | | 1.26 | 0.00 | | 0.00 |
| K12 + R0052 | 0.00 | | NA | 3.25 | | 0.25 | 3.25 | | 0.00 | 2.75 | | 0.41 | 0.00 | | 0.00 |
| K12 + SD5846 | 0.00 | | NA | 2.25 | | 0.15 | 2.25 | | 0.00 | 2.75 | | 1.10 | 0.00 | | NA |
| K12 + Lp2001 | 0.00 | | US | 3.00 | | 0.24 | 3.00 | | 0.20 | 2.67 | | 2.67 | 0.00 | | 0.00 |
| M18 + LAFTI L10 | 0.00 | | NA | 5.00 | | 0.92 | 5.00 | | 1.50 | 9.50 | | 2.20 | 2.50 | | 0.44 |
| M18 + R0052 | 0.00 | | NA | 4.25 | | 1.76 | 4.25 | | 0.61 | 4.50 | | 0.61 | 0.00 | | 0.00 |
| M18 + SD5846 | 0.00 | | NA | 0.00 | | 0.00 | 0.00 | | NA | 0.00 | | 0.00 | 0.00 | | NA |
| M18 + Lp2001 | 5.75 | | US | 11.00 | | 5.81 | 11.00 | | 9.19 | 10.25 | | 5.86 | 8.50 | | US |
| LAFTI L10 + R0052 | 0.00 | | NA | 6.50 | | 1.02 | 6.50 | | 0.19 | 5.00 | | 0.49 | 4.25 | | 0.37 |
| LAFTI L10 + SD5846 | 5.00 | | US | 14.50 | | 1.77 | 14.50 | 0.01 | 3.69 | 14.75 | 0.03 | 2.43 | 12.50 | | 2.19 |
| LAFTI L10 + Lp2001 | 13.00 | <0.0001 | US | 20.14 | <0.0001 | 3.44 | 20.14 | <0.0001 | 3.94 | 19.29 | <0.0001 | 4.22 | 23.86 | <0.0001 | 4.18 |
| R0052 + SD5846 | 0.00 | | NA | 6.50 | | 1.26 | 6.50 | | 1.64 | 9.75 | | 1.06 | 9.50 | | 1.68 |
| R0052 + Lp2001 | 0.00 | | NA | 9.25 | <0.01 | 3.29 | 9.25 | 0.05 | 1.51 | 13.75 | 0.01 | 1.79 | 9.25 | 0.05 | 1.63 |
| SD5846 + Lp2001 | 3.50 | | US | 1.75 | | 0.38 | 1.75 | | 0.88 | 5.00 | | 1.43 | 2.50 | | US |

Fig. 7

| Strain | Exp. 1 | Exp. 2 | Exp. 3 |
|---|---|---|---|
| S. salivarius K12 | - | - | - |
| S. salivarius M18 | +++ | +++ | +++ |
| S. thermophilus R0083 | + | + | ++ |
| S. thermophilus St-21 | + | ++ | - |
| L. rhamnosus GG | +++ | +++ | +++ |
| L. plantarum Lp-2003 | - | - | - |
| L. paracasei Lp-37 | +++ | +++ | +++ |
| L. salivarius Ls-33 | + | ++ | +++ |
| L. acididophilus La-14 | + | +++ | ++ |
| L. reuteri Lru-1038 | + | ++ | + |
| L. plantarum Lp-115 | - | - | - |
| L. rhamnosus Lr-32 | +++ | +++ | +++ |
| L. helveticus R0052 | +++ | +++ | +++ |
| L. acidophilus (LAFTI) L10 | + | + | + |
| L. casei Lc-11 | - | + | - |
| B. lactis Bl-04 | + | ++ | + |
| B. breve Bl-03 | + | + | - |
| B. bifidum R0071 | +++ | +++ | +++ |
| B. longum R0071 | +++ | +++ | +++ |
| B. longum R0175 | +++ | +++ | +++ |
| B. longum Bl-05 | +++ | +++ | +++ |

Fig. 8

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
actacacttt cgggtggctt gg                                              22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
cagtataagc gccagtttca tc                                              22
```

ORAL COMPOSITIONS

CROSS-REFERENCE TO RELATED APPLICATIONS

This application claims the benefit of U.S. Provisional Patent Application U.S. Ser. No. 61/843,158 filed Jul. 5, 2013, the entire contents of which is herein incorporated by reference.

SEQUENCE LISTING

The instant application contains a Sequence Listing which has been submitted in ASCII format via EFS-Web and is hereby incorporated by reference in its entirety. Said ASCII copy, created on Jan. 4, 2016, is named pctca2014050642_seql.txt and is 673 bytes in size.

FIELD

The present invention relates to probiotic compositions for oral administration. In particular, the present invention relates to probiotic compositions with beneficial effects, such as improved health, especially oral health, and methods of administration of the compositions.

BACKGROUND

An oral cavity, e.g. mouth, shelters numerous and varied microbial flora. When the equilibrium is compromised and when an imbalance appears amongst the indigenous bacteria, pathologies such as dental caries or periodontitis can occur. Probiotics are live microorganisms that may confer a health benefit on the host. The beneficial effects of probiotic therapy are achieved in part through the modulation of existing microbial flora associated with the host, thus attaining a balanced and healthy microbes-host relationship. In relation to the oral cavity, probiotic compositions may help to restore a balanced bacterial population, thereby improving oral health.

Dental caries is a ubiquitous infectious disease typically transmitted through caregivers in childhood, which persists throughout life or until complete edentulism. Dental caries is predominantly managed through antimicrobial preventative approaches like tooth brushing or flossing which are effective largely because of their antimicrobial action. Recent advances in Cariology have led to a better understanding of the broader microecological context of caries formation, which presents opportunities for new microbial based prophylactic treatment strategies and technologies to be applied in caries management.

The infection of the initiating pathogenic bacteria involved in caries are mutans streptococci group bacteria, most notably *Streptococcus mutans* that encapsulates within a biofilm of insoluble exopolysaccharides self-generated from sucrose. This adherent plaque, provides and ecological niche where the pathogenic bacteria thrive and produce various organic acids from carbohydrates that progressively dissolves the tooth minerals. The more contemporary understanding of caries development now includes the context of microbial, ecological, and environmental factors, where an alteration or imbalance in the microfloral ecology predisposes one to caries formation. To this end, probiotic therapies have been suggested as having potential to be an effective means of regulating *S. mutans* and the oral microflora (Caglar 2005a; Saha 2012; Tagg 2003) and there has been significant clinical research of individual strains' potential use as probiotics (Näse 2001; Taipale 2012; Keller 2011; Stecksén-Blicks 2009; Burton 2013; Caglar 2008; Caglar 2006; Caglar 2005b).

The ostensible mechanism by which various strains combat dental caries varies case by case. For example some strains have anti-*S. mutans* activity by aggregating with the *S. mutans*, while others directly kill or inhibit *S. mutans* by secreting specific bacteriocins, and others still colonize the plaque and compete with *S. mutans* for its ecological niche. The potential therefore exists for complementary synergistic effects of combining these mechanisms. For another example, two probiotic strains may secrete different bacteriocins that, because of their varying biochemical target within the *S. mutans*, may have greater combined *S. mutans* killing effect than either on their own.

Probiotic compositions may also be enhanced in certain circumstances through the addition of prebiotics to the composition. A prebiotic "feeds" microbial flora, so as to enhance a beneficial bacterial subpopulation; a probiotic adds beneficial cultures to populations of microbial flora. The term "synbiotic" describes a composition that contains both prebiotics and probiotics, for example, one that contains both fructooligosaccharides (FOS) (a prebiotic) and bifidobacteria (a probiotic). Research in the area is devoted to the synergy between the types of ingredients to obtain a better understanding of how growth and survival of probiotics may be enhanced by the presence of complementary prebiotic ingredients.

Although a large number of probiotic compositions are known, each composition has unique characteristics and particular health benefits. One example of a probiotic composition with a benefit for oral health is described in commonly-owned U.S. Provisional application U.S. Ser. No. 61/674,390 filed Jul. 22, 2012, which discloses a probiotic combination including *Streptococcus salivarius* K12® (BLIS K12®) and at least five *Lactobacillus* bacteria.

However, there is always a need for improved formulations of probiotic compositions, particularly formulations that result in one or more of improved oral health, improved oral colonization, improved efficacy, improved shelf-life, efficacy for different and specific oral diseases, and additional improvements, as well as methods of administration or uses thereof.

SUMMARY

In one aspect of the invention there is provided a composition for use in oral hygiene, comprising an oral hygiene effective amount of a probiotic, the probiotic comprising a *Lactobacillus helveticus* strain.

In a second aspect of the present invention, there is provided a composition for use in oral hygiene, comprising an oral hygiene effective amount of a probiotic, the probiotic comprising a *Lactobacillus helveticus* strain and a *Lactobacillus plantarum* strain.

In a third aspect of the present invention, there is provided a composition for use in oral hygiene, comprising an oral hygiene effective amount of a probiotic, the probiotic comprising a *Lactobacillus helveticus* strain and *Bifidobacterium longum* SD5846.

In a fourth aspect of the present invention, there is provided a composition for use in treating or preventing dental caries, comprising a dental caries preventing effective amount of a probiotic, the probiotic comprising *Lactobacillus plantarum* SD5870.

In a fifth aspect of the present invention, there is provided a composition for use in treating or preventing dental caries, comprising a dental caries preventing effective amount of a probiotic, the probiotic comprising *Bifidobacterium longum* SD5846.

In a sixth aspect of the present invention, there are provided uses of the aforementioned probiotics for oral hygiene.

In a seventh aspect of the present invention, there are provided uses of the aforementioned probiotics for the preparation of a medicament for oral hygiene.

In an eighth aspect of the present invention, there is provided a method of treating or preventing an oral condition or disease in a subject, comprising orally administering an aforementioned probiotic to the subject.

In an ninth aspect of the present invention, there is provided a commercial package comprising an aforementioned probiotic and instructions for its use in oral hygiene.

The probiotic comprises or consists essentially of a *Lactobacillus helveticus* strain. The probiotic may comprise or consist essentially of a *Lactobacillus helveticus* strain and one or more other probtiotic bacteria, preferably from the lactobacilli, bifidobacteria and/or streptococci genii, more preferably one or more other lactobacilli, yet more preferably one other *lactobacillus*. The probiotic may comprise or consist essentially of both a *Lactobacillus helveticus* strain and a *Lactobacillus plantarum* strain, especially *Lactobacillus plantarum* SD5870 (known commercially as *Lactobacillus plantarum* Lp-2001). The phrase "consists essentially of" indicates that other probiotic bacteria are not present, or are present in inconsequential amounts. The *Lactobacillus helveticus* strain preferably comprises *Lactobacillus helveticus* LAFTI L10, *Lactobacillus helveticus* R0052 or a mixture thereof. The *Lactobacillus helveticus* strain more preferably comprises *Lactobacillus helveticus* LAFTI L10.

For treating or preventing dental caries specifically, the probiotic may alternatively comprise *Lactobacillus plantarum* SD5870 or *Bifidobacterium longum* SD5846. The probiotic preferably comprises *Lactobacillus plantarum* SD5870 in combination with one or both of *Streptococcus salivarius* M18 and *Streptococcus salivarius* K12. Preferably, the probiotic consists essentially of *Lactobacillus plantarum* SD5870, or consists essentially of *Lactobacillus plantarum* SD5870 and one or both of *Streptococcus salivarius* M18 and *Streptococcus salivarius* K12 such that other probiotic bacteria are not present, or are present in inconsequential amounts.

Oral hygiene comprises the prevention or treatment of conditions or diseases of an oral cavity. Such conditions or diseases include, for example, dental caries (cavities), halitosis, gingivitis, mouth ulcers including aphthous stomatitis (canker sores), candidiasis and periodontal diseases. In one aspect of the invention, *Streptococcus mutans* population in the oral cavity is suppressed leading to better oral health. In a particularly preferred embodiment, dental caries is prevented. Subjects for which this invention is useful include, for example, mammals. Subjects may include primates, humans or domesticated animals. Some examples of domesticated animals are dogs, cats and horses.

The composition may comprise from about 0.0001% to about 100% by weight of the probiotic, based on total weight of the composition. Optionally, the probiotic may be from about 0.001% to about 50% by weight, or from about 0.001% to about 10% by weight, or from about 0.001% to about 5% by weight of the composition. Oral hygiene effective amounts of the probiotic in the composition depend to some extent on the age of the subject, the type of probiotic bacteria, dosing frequency, dosage form, administration method and variability in the subjects' commensal oral microflora. For example, dosages of the probiotic in a range of about $10^7$ to $10^{11}$ colony forming units (CFU) are generally suitable; particularly for lozenges, dosages of the probiotic in a range of about $10^8$ to $10^{10}$ CFU per lozenge are preferred, the optimal amount depending on the strain or strains of probiotic in the composition and the frequency of administration, which can vary from 1 to 4 lozenges per day. Administration of the probiotic may be performed at any convenient time, for example during or after teeth brushing, or during or after meals.

Compositions comprise the probiotic and may comprise other ingredients generally known in the art, for example one or more remineralization agents, prebiotics, carriers, diluents, excipients and the like. The other ingredients are preferably pharmaceutically acceptable or at least acceptable for use in the oral cavity.

*S. mutans* functions in decaying the tooth matrix through the secretion of acids that dissolve minerals calcium and phosphate. After several months of acid secretion, the demineralization will then spread to the enamel and eventually to the dentine. Although reversible at this phase, further progression will lead to cavity formation, and necessitate tooth restoration. Saliva plays an important role not only as a natural buffer to the offending acids, but also as a source of calcium and phosphate for remineralization of the teeth, naturally arresting or even reversing the pathology. Dental caries formation then is a dynamic equilibrium of demineralization by pathogenic bacteria and remineralization. Interventions and prophylactic treatments often focus on tipping the balance towards remineralization by adding agents to this effect. Remineralization agents include, for example, casein phosphate peptide-amorphous calcium phosphate (CPP-ACP), β-tricalcium phosphate, nanoparticles of amorphous calcium phosphate (NACP), hydroxyapitite, calcium glycerophosphate or other variants of calcium and phosphate. The re-mineralization agent can be added in an amount of from 1 to 10 wt % of the composition, preferably from 1 to 4 wt %. Fluoride is also added to many dental products as it is an effective catalyst of remineralization, and incorporates into the crystalline structure resulting in a more resistant tooth surface than the original. Notably casein phosphate peptide-amorphous calcium phosphate (CPP-ACP) (see U.S. Pat. No. 7,491,694, the disclosure of which is herein incorporated by reference) is particularly effective because the bound peptide derived from a milk protein binds and stabilizes the calcium phosphate into a soluble amorphous from that is readily bioavailable. The combination of a probiotic formulation that prevents the demineralization, together with a remineralization agent, especially CPP-ACP, would be expected to have even greater effectiveness in the prophylactic treatment of dental caries.

Inclusion of prebiotics in the composition enhances probiotic effectiveness in certain circumstances. A prebiotic mainly functions to feed microbial flora. The term "synbiotic" describes a composition that contains both prebiotics and probiotics. Some examples of prebiotics that may be useful in the present invention include, for example, mono-, di- and oligo-saccharides such as manose fructans, fructooligosaccharides (FOS), xylooligosaccharides (XOS), polydextrose and galactooligosaccharides (GOS), lactulose, tagatose, inulin, maltodextrin, lactitol and mixtures thereof. In general, the amount of prebiotic used is much greater than the amount of probiotic, for example gram amounts of prebiotic may be used for milligram amounts of probiotic.

Carriers, diluents and excipients for oral compositions are generally known the art and include, for example, absorbents, acidifying agents, alkalizing agents, binders, buffers, coatings, colors, controlled-release agents, controlled-release carriers, diluents, disintegrants, effervescent agents, flavors, glidants, lubricants, plasticizers, solubility enhancers, wetting agents, surfactants, preserving agents, sweetening agents, flavouring agents, etc. Some specific examples include lactose, dextrose, fructose, sucrose, sorbitol, mannitol, starches, gum acacia, calcium phosphate, alginates, tragacant, gelatine, calcium silicate, polyvinylpyrrolidone, cellulose (e.g. microcrystalline cellulose), water syrup, water, water/ethanol, water/glycol, water/polyethylene glycol, propylene glycol, methyl cellulose, methylhydroxybenzoates, propyl hydroxybenzoates, talc, magnesium stearate, mineral oil or fatty substances such as hard fat or suitable mixtures thereof.

A particularly preferred class of excipients is sugar substitutes, which act as sweeteners with a reduced or negligible effect on blood glucose levels. Preferably, the sugar substitutes are non-cariogenic. Such sugar substitutes include, for example, sugar alcohols (e.g. isomalt), stevia, aspartame, sucralose, neotame, acesulfame potassium and saccharin. Stevia and isomalt are of particular note. Stevia is based on steviol glycosides and comprises an extract of the plant *Stevia rebaudiana*. Isomalt is an equimolar mixture of two disaccharides, each composed of two sugars glucose and mannitol (α-D-glucopyranosido-1,6-mannitol) and also glucose and sorbitol (α-D-glucopyranosido-1,6-sorbitol). Isomalt in particular improves stability of the compositions of the present invention. Certain sugar substitutes (e.g. isomalt) may also be considered to be prebiotics.

Compositions of the present invention may be administered to the subject orally in oral or topical dosage forms. Suitable dosage forms include, for example, tablets (e.g. effervescent tablets and/or multi-layered tablets), pills, powders, lozenges (including multi-layered lozenges), sachets, cachets, elixirs, suspensions, emulsions, solutions, syrups, aerosols, capsules, pastes (e.g. toothpaste), food and confectionary (e.g. chewing gum). Formulation of such dosage forms is well known in the art. Compositions of the present invention have good stability maintaining effective CFU count of the probiotic strains over a period of at least 24 months, even over a period of at least 30 months, at room temperature (20-25° C.). Shelf life can be extended beyond 36 months in certain storage conditions (e.g., refrigerated conditions at 2-8° C.) and/or various delivery systems such as sachets/powder sticks.

The composition may be provided in the market place in the form of a commercial package together with instructions for use of the composition for oral hygiene. Commercial packages include, for example, bottles, jars, blister packs, boxes, etc. Instructions may be provided, for example, in visual or audio forms, for example, in writing, in pictures, on sound and/or video recording media, or combinations thereof.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 7 depicts a table showing synergistic antagonism against strains of *S. mutans* for different combinations of probiotic strains with anti-microbial characteristics. Comparison was made to component strains individually by one-way ANOVA with data from at least four individually repeated experiments.

FIG. 8 depicts a table showing comparison of the relative production of hydrogen peroxide of probiotic strains. +++ within 24 hours, ++ within 48 hours, + within 72 hours, and—no production.

DETAILED DESCRIPTION

Throughout the specification reference is made to genus/species names and to strain designations. From time to time the classification of organisms changes and any given organism may be assigned a different name and/or strain designation. The probiotic organisms referred to herein have certain genomes that would remain the same whether or not the name and/or strain designation of the organisms changes. From the genome, one skilled in the art can readily determine whether any given organism, whatever name and/or strain designation it carries, is encompassed by the present description.

EXAMPLE 1

*S. Mutans* Isolation and DNA Extraction

Plaque was collected using sterile probes and spread directly onto mitis salivarius-bacitracin *S. mutans* selective agar from 4 different subjects, and then incubated for 48 hours at 37° C. in microaerophilic conditions. Individual colonies were then quadrant streaked onto BHYE plates and then incubated again for 48 hours at 37° C. in microaerophilic conditions. Subsequent genotyping was undertaken on the isolated colonies to confirm their species. Bacterial DNA extracted using InstaGene Matrix (BioRad) similar to manufacturer's instructions. Briefly, a single colony was picked and dispersed in 1 mL of sterile $H_2O$. This mix was then centrifuged for 1 minute at 10,000 rpm and the supernatant discarded. To the pellet was added 200 μL of IntaGene Matrix, the samples were vortexed quickly and incubated at 55° C. for 20 minutes in a water bath. Samples were then removed and incubated in a boiling water bath for 30 minutes. The samples were then vortexed again and then centrifuged for 3 minutes at 10,000 rpm. Supernatants were collected and stored at −20° C. until used for PCR.

All PCR reagents were obtained from Invitrogen. Samples of extracted DNA were subjected to PCR in a reaction mixture containing 1× PCR buffer, 15 mM $MgCl_2$, 200 mM dNTP mix, 10 μM MUT-F primer, 10 μM MUT-R primer, 5 U of Taq DNA polymerase, 10 μL of DNA template, and dd$H_2O$ up to a final volume of 50 μL. The primers amplify a 517-bp DNA region coding the gtfB extracellular glucosyltransferase of S. mutans (Oho 2000).

```
                                            (SEQ ID NO: 1)
MUT-F: 5'-ACT ACA CTT TCG GGT GGC TTG G-3'

(SEQ ID NO: 2)
MUT-R: 5'-CAG TAT AAG CGC CAG TTT CAT C-3'
```

The thermocycling conditions were an initial denaturation at 95° C. for 1 minute, followed by 30 cycles of denaturation at 95° C. for 30 seconds, annealing at 59° C. for 30 seconds, and extension at 72° C. for 1 minute. A final extension step at 72° C. for 5 minutes was included. PCR products were then mixed with DNA loading buffer and separated with a 1.5% agarose gel with 0.05% EtBr at 100 V for 45 minutes, and imaged under UV light excitation.

EXAMPLE 2

Deferred Antagonism

Figure 1:
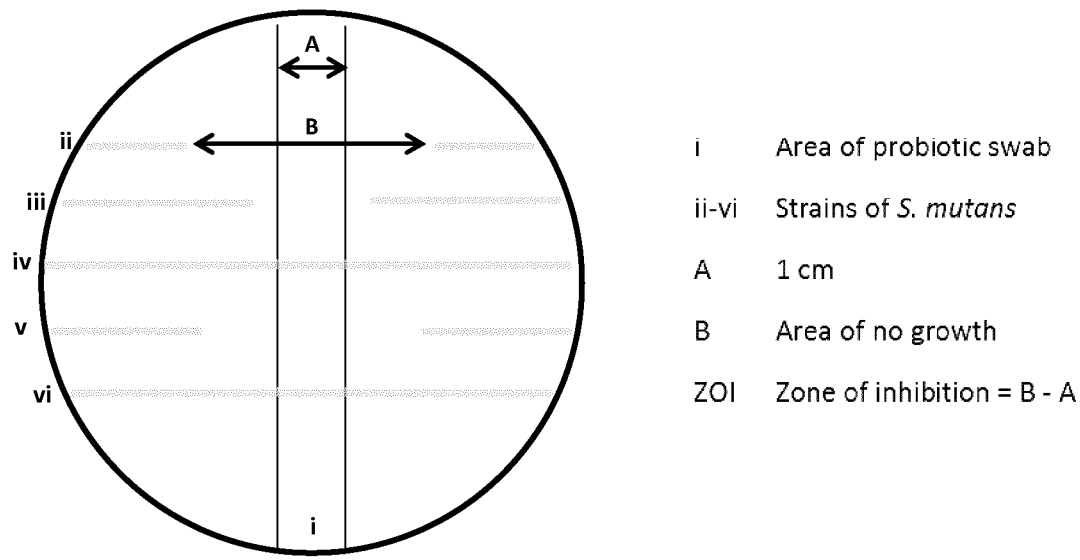
FIG. 1 depicts a schematic diagram of culture plates showing bacterial swabbing zones and how zones of inhibition (ZOIs) are determined.

To test the antagonism of the probiotics against S. mutans, deferred antagonism was undertaken essentially as previously performed by Tagg and Bannister (Tagg 1979). Liquid cultures were inoculated into MRS for either lactobacilli or bifidobacteria, and BHYE for streptococci, and then incubated overnight at 37° C. in microaerophilic conditions. Referring to FIG. 1, the overnight suspension was then swabbed onto a BHI or CB plate with 0.1% (w/v) $CaCO_3$ in a measured 1 cm wide streak using sterile cotton swabs. BHI plates contained 18.5 g brain heart infusion (BHI, Difco), 7.5 g agar (Fisher) and 1 g $CaCO_3$ (Sigma). CB plates contained 22 g Columbia blood (Difco), 7.5 g agar (Fisher) and 1 g $CaCO_3$ (Sigma). The plates were then incubated at 37° C. in microaerophilic conditions. After 48 hours the bacterial growth was scraped off with a glass microscope slide, and the plate re-sterilized with chloroform vapors for 20 minutes. Overnight suspensions of the type strain S. mutans ATCC25175 and 4 fresh isolates were then streaked across perpendicularly, and the plates were re-incubated. After 48 hours the zone of inhibition (ZOI) was calculated as the distance between the two areas of bacterial growth, minus 1 cm where the probiotic was directly plated. Statistics was performed using Prism 4 (GraphPad). One-way ANOVAs were used to compare between specific probiotics and probiotic combinations. Synergism was calculated as a synergistic quotient, which is the sum of the individual treatments divided by the combined treatment. A values >1 indicate synergism of the combination (Wang 2012).

Figure 2:
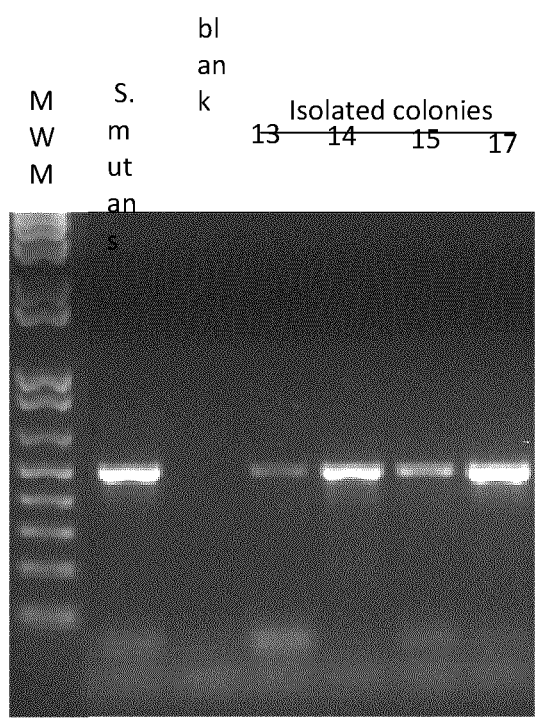
FIG. 2 depicts a 1.5% agarose gel of PCR amplicons of a species specific DNA segment of the *S. mutans* chromosome. Type strain *S. mutans* 25175 was used as a positive control.

To determine strains with probiotic potential in dental caries, an S. mutans antagonism screening was undertaken for many commercialized strains of probiotics. Firstly, as described in Example 1, fresh isolates of the pathogen were obtained by plating plaque samples from 4 individuals onto S. mutans selective mitis salivarius-bacitracin agar plates. Colonies were genotyped for the presence of an S. mutans specific marker sequence, which was compared against the type strain S. mutans ATCC 25175 (FIG. 2). Four isolates were selected (1 per subject).

Deferred antagonism assays against these 4 isolates and S. mutans 25175 was undertaken on two media types to rapidly screen probiotic strains with any antagonism. Table 1 indicates the presence or absence of a zone of inhibition (ZOI) for any replicate, and for any of the 5 strains assayed in these experiments. Strains Streptococcus salivarius K12, Streptococcus salivarius M18, Lactobacillus plantarum SD5870, L. helveticus R0052, and Bifidobacteria longum SD5846 (known commercially as Bifidobacteria longum Bl-05) were observed to have antagonism on both agar types, while for Lactobacillus helveticus LAFTI L10 antagonism was only apparent on BHI agar. BHI agar was therefore used in subsequent quantitative deferred antagonism experiments. To quantify the antagonism, the experiment was repeated for each probiotic bacteria in at least four and as many as eight separate experiments, and the zone of inhibition was specifically measured. Equal mixtures of all probiotic bacterial strains in all possible combinations of 2 were assessed to test for potential synergistic effects. The ZOI of five pathogenic strains was measured and averaged across four experiments. The results are indicated in FIG. 3 to FIG. 6.

Figure 3:
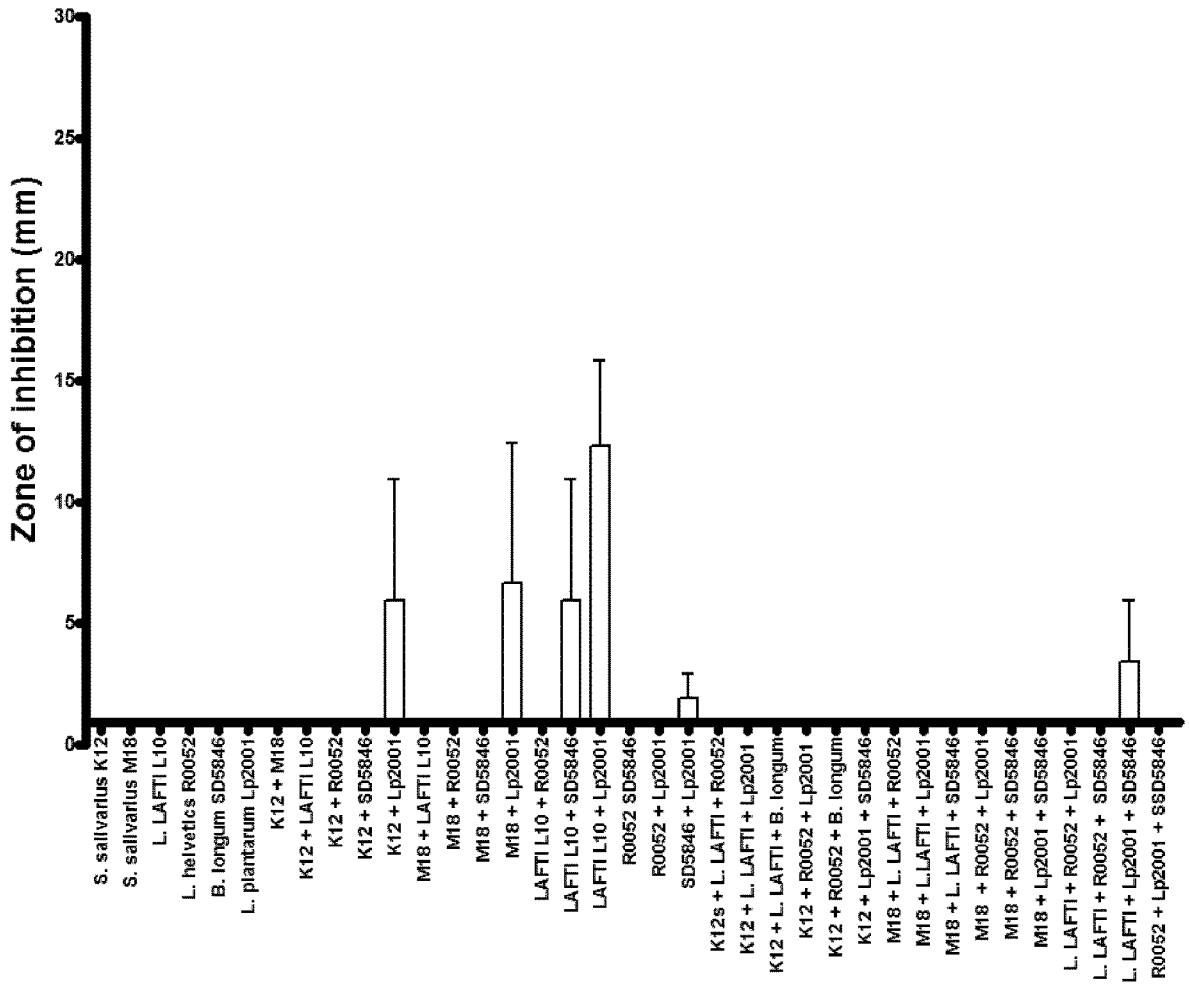
FIG. 3 depicts a graph showing quantification of deferred antagonism experiments of probiotics individually and in all possible combinations of two against *S. mutans* 25175. Experiments were repeated at least 4 times using BHI agar pH balanced with 0.1% $CaCO_3$.
Figure 4:
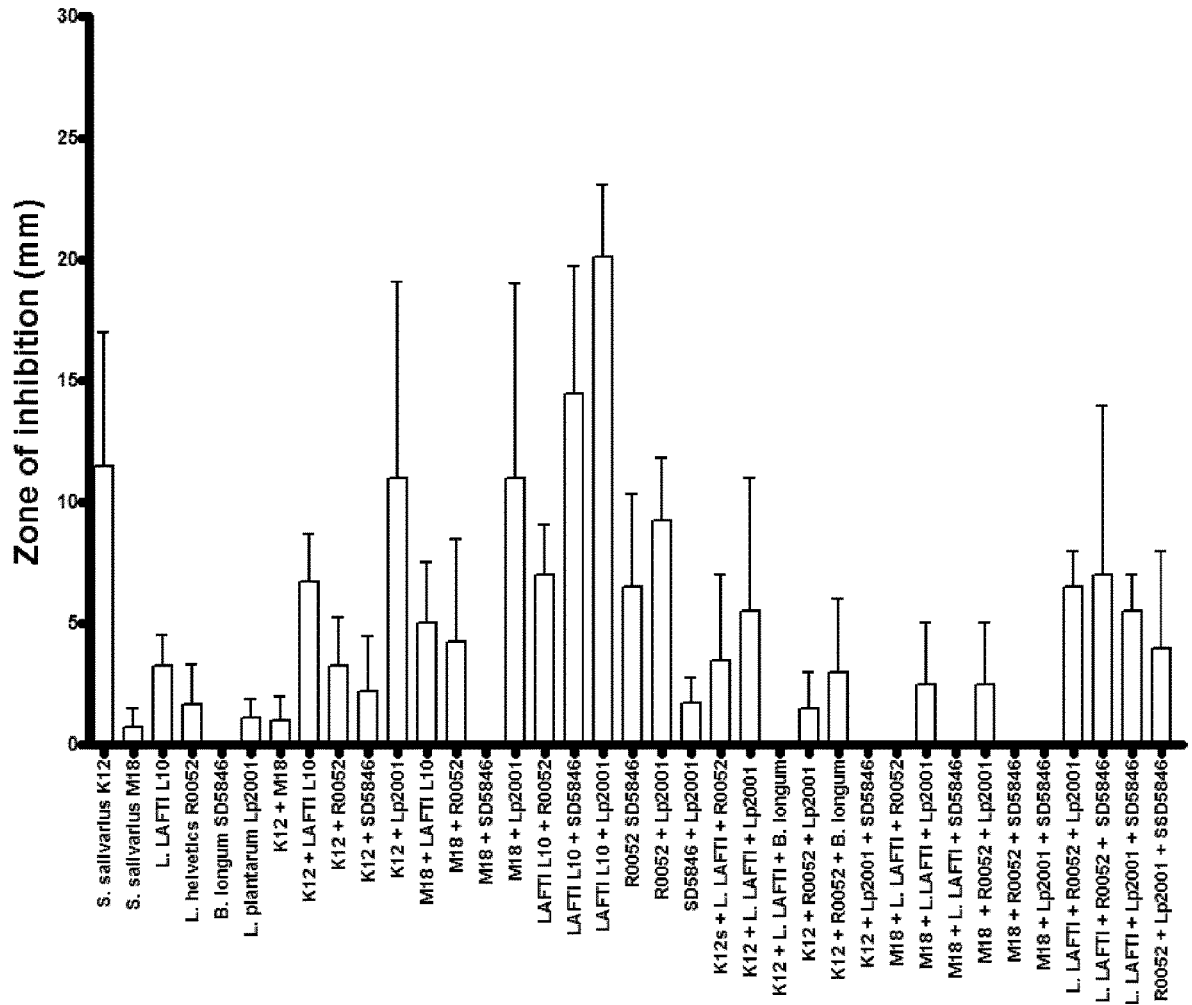
FIG. 4 depicts a graph showing quantification of deferred antagonism experiments of probiotics individually and in all possible combinations of two against freshly isolated *S. mutans* 13. Experiments were repeated at least 4 times using BHI agar pH balanced with 0.1% $CaCO_3$.
Figure 5:
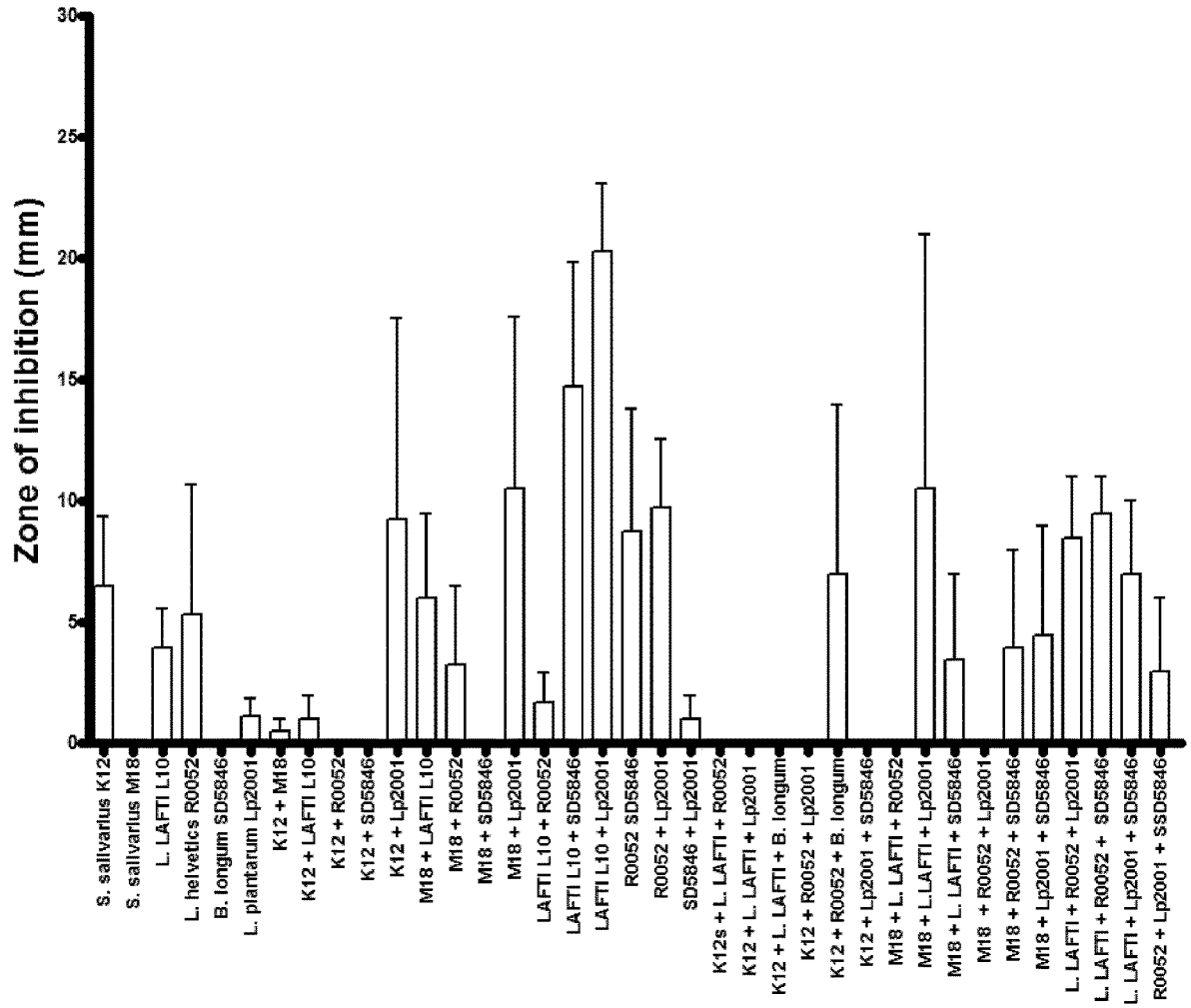
FIG. 5 depicts a graph showing quantification of deferred antagonism experiments of probiotics individually and in all possible combinations of two against freshly isolated *S. mutans* 14. Experiments were repeated at least 4 times using BHI agar pH balanced with 0.1% $CaCO_3$.
Figure 6:
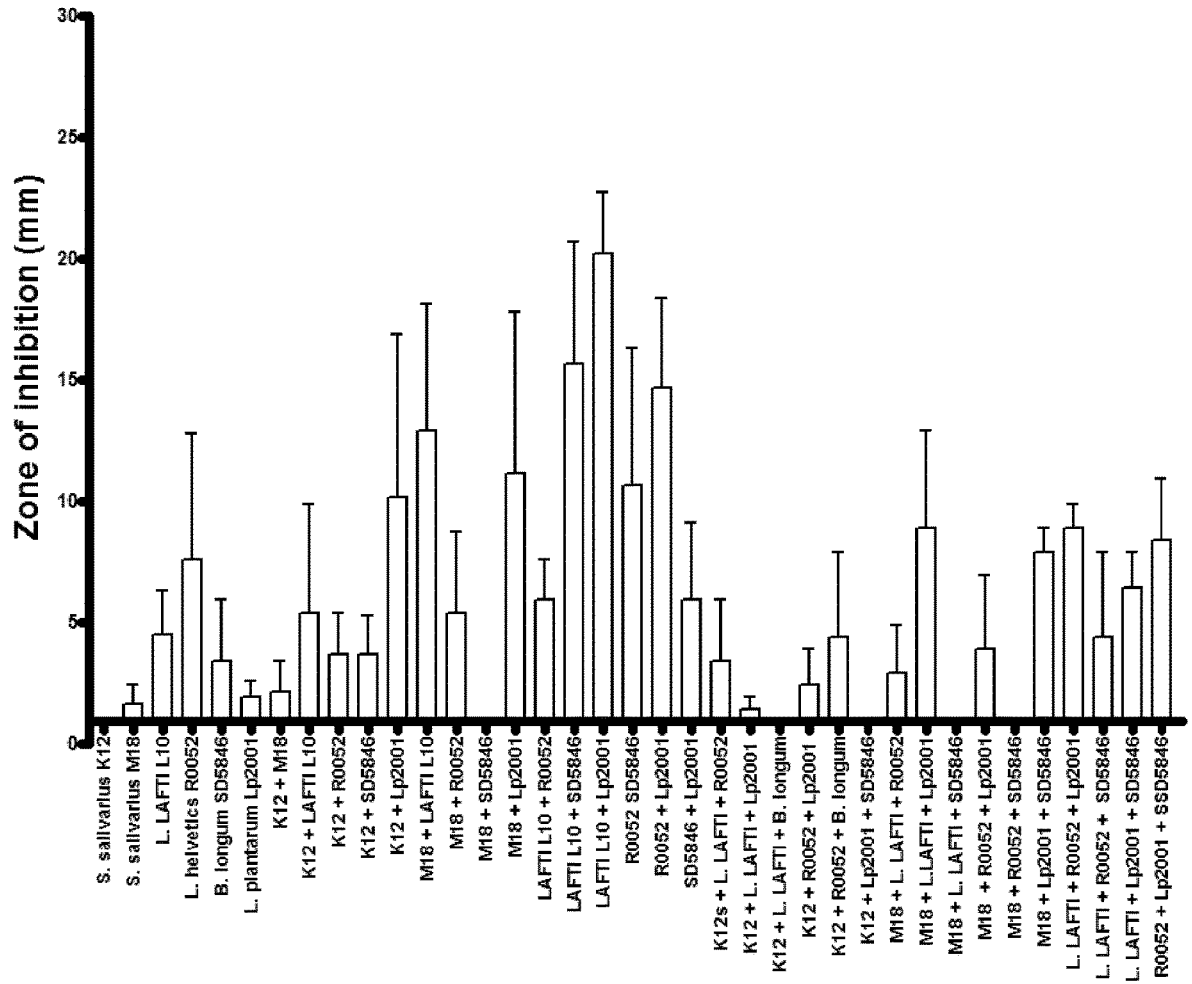
FIG. 6 depicts a graph showing quantification of deferred antagonism experiments of probiotics individually and in all possible combinations of two against freshly isolated *S. mutans* 15. Experiments were repeated at least 4 times using BHI agar pH balanced with 0.1% $CaCO_3$.

In general, the culture collection strain of S. mutans proved to be much more resistant to antagonistic factors secreted by the probiotics compared to fresh isolates (FIG. 3). For example in single probiotic experiments, no antagonism was observed at all for the S. mutans 25175, while for S. mutans 13, all 6 probiotics except B. longum SD5846 were antagonistic. As a single strain L. helveticus LAFTI L10 and L. helveticus R0052 were able to antagonize all four freshly isolated S. mutans, while S. salivarius K12, and L. plantarum SD5870 antagonized three of four. S. salivarius M18 antagonized two of the four pathogenic isolates, and B. longum SD5846 only one, and the average ZOI for these were, in all cases, comparatively weaker than other probiotic strains.

TABLE 1

Presence or absence of a ZOI based on qualitative observations of deferred antagonism assays against five S. mutans strains.

| Strain | CB | BHI |
|---|---|---|
| S. salivarius K12 | + | + |
| S. salivarius M18 | + | + |
| S. thermophilus R0083 | − | − |
| S. thermophilus St-21 | − | − |
| L. rhamnosus GG | − | − |
| L. plantarum SD5870 | + | + |
| L. paracasei Lp-37 | − | − |
| L. salivarius Ls-33 | − | − |
| L. acididophilus La-14 | − | − |
| L. reuteri Lru-1038 | − | − |
| L. plantarum Lp-115 | − | − |

TABLE 1-continued

Presence or absence of a ZOI based on qualitative observations of deferred antagonism assays against five S. mutans strains.

| Strain | CB | BHI |
|---|---|---|
| L. rhamnosus Lr-32 | − | − |
| AAP-2 | − | − |
| L. helveticus R0052 | + | + |
| L. helveticus LAFTI L10 | − | + |
| L. casei Lc-11 | − | − |
| B. lactis BI-04 | − | − |
| B. breve BI-03 | − | − |
| B. bifidum R0071 | − | − |
| B. longum R00175 | − | − |
| B. longum SD5846 | + | + |

The average ZOI were in many cases greater when two strains were combined together in equal amounts and certain bacteria appeared to combine better than others. For isolate S. mutans 15 for example (FIG. 6), of the 15 possible combinations of 2 strains, 7 were greater than the ZOI of L. helveticus R0052, the greatest inhibiting individual probiotic. Of these 7 combinations, six contained either a L. helveticus LAFTI L10 or a L. plantarum SD5870. This proved true across all pathogenic strains; in each instance of inhibiting S. mutans isolates 13, 14, 15, and 17, or even S. mutans 25175, the 4 largest ZOI were always combinations containing either a L. helveticus LAFTI L10 or a L. plantarum SD5870.

FIG. 7 indicates the average zone of inhibition (ZOI) together with the calculated synergism of the antagonism. Significant difference of the ZOI as calculated by 1-way Anova for combinations compared to its component strains individually is indicated. The synergistic quotient (SQ) indicates the relative synergism by dividing the ZOI for combinations of probiotics by the sum of their component ZOI measured individually. Combinations with greater than 50% synergism (SQ >1.5) are indicated in bold. NA indicates no antagonism, while US indicates undetermined synergism, as antagonism was only ever observed in combination. The combination of L. helveticus LAFTI L10 with B. longum SD5846 and the combination of L. plantarum SD5870 with L. helveticus R0052 were both significantly more antagonistic against strains of S. mutans than their individual components. The combination of L. helveticus LAFTI L10 with B. longum SD5846 was very synergistic with US, 1.8, 3.7, 2.4, and 2.2 when tested against S. mutans strains 25175, 13, 14, 15, and 17, respectively. L. plantarum SD5870 with L. helveticus R0052 was also synergistic, exhibiting an SQ of NA, 3.3, 1.5, 1.8, and 1.6, respectively.

Interestingly, however, component bacteria from each of these two synergistic combinations (L. helveticus LAFTI L10 and L. plantarum SD5870) resulted in particularly strong activity, and synergism when combined together. The ZOI for these 2 strains combined was the highest antagonism by a significant margin for all five strains of S. mutans. The ZOI for L. helveticus LAFTI L10 and L. plantarum SD5870 was in fact higher than the ZOI for the two strains individually added together for all strains of S. mutans, which proved highly significant by 1-way ANOVA. For S. mutans 25175 there was no inhibition at all by either probiotic strain individually, but very significant inhibition (about 20 mm) when the two strains were combined together. This is strongly suggestive of synergistic activity between the probiotics, and in fact the synergistic quotients were US, 3.4, 3.9, 4.2 and 4.2 for strains of S. mutans 25175, 13, 14, 15, and 17, respectively.

EXAMPLE 3

Hydrogen Peroxide Production

To test hydrogen peroxide production, a commonly used methodology was employed that is very similar to that recently used by Kang et al (Kang 2011). Essentially, standard agar growth media (MRS for either lactobacilli or bifidobacteria, and BHYE for streptococci) was modified by the addition of 0.25 mg/mL 3,3',5,5'-tetramethylbenzidine (TMB) and 0.1 ng/mL peroxidase. Briefly, 0.125 g of TMB and 5 mg of peroxidase was dissolved in 1 mL of dimethyl sulfoxide (DMSO) and water respectively. These solutions were sterilized using 0.2 μm syringe filters and added to 0.5 of liquid agar media immediately following post autoclave cooling to <50° C. Plates were then poured. Individual colonies of probiotic were picked from a stock plate, and streaked directly onto TMB/peroxidase agar and standard agar control plates using an inoculation loop. Plates were then left at 37° C. in microaerophilic conditions for 72 hours. The colonies and surrounding agar were assessed for any change in color to either blue or red every 24 hours by comparing to a normal MRS or BHYE streaked control plate. The experiment was repeated three times.

Since many lactobacilli produce hydrogen peroxide as an antagonistic agent against surrounding bacteria, the hydrogen peroxide production of the strains was assayed. It was confirmed that 10 of the 11 lactobacillus strains tested produced some hydrogen peroxide. S. salivarius did not while the two S. thermophilus and all 5 of the bifidobacteria produced varying degrees of $H_2O_2$ (FIG. 8). All strains that were observed to have S. mutans antagonism were all among the fastest to produce $H_2O_2$, having been observed to do so within 24 hours of plating, with the exception of S. thermophilus.

EXAMPLE 4

Cell Surface Adhesion

Cell culture reagents were obtained from GIBCO unless otherwise stated. The immortalized human bronchial epithelial cell line 16HBE14o- was grown in MEM media supplemented with 10% FBS and 2 mM L-glutamine, and maintained using standard cell culture procedures at 37° C. and 5% $CO_2$. Cells were seeded in wells of a tissue-culture treated 24-well plate at a concentration of $1 \times 10^5$ cells/well and allowed to grow to confluency (about 48 hours, approximately $5 \times 10^5$ cells/well). Cell media was then aspirated and replaced with 500 μL of fresh media containing 100-fold dilutions of the various stationary phase bacterial cell suspensions, which were grown overnight in MRS (lactobacilli and bifidobacteria) or BHYE (streptococci). Plates were then incubated at 37° C. and 5% $CO_2$. After 5 hours, the culture media was aspirated and the monolayers washed thoroughly three times with PBS to remove non-loosely adherent bacteria. Eukaryotic cells were then disrupted by adding Triton™ X-100 to a final concentration of 0.1%. Enumeration of the remaining adherent CFUs contained in the lysis suspension was then undertaken by drop plate method. Serial dilutions up to $10^{-6}$ were made in a 96 well plate in 10-fold steps, with 10 μL of the various dilutions then spotted in triplicate onto appropriate agar (MRS for lactobacilli and bifidobacteria, and BHYE for streptococci).

The agar plates were incubated at 37° C. in microaerophilic conditions for 24 hours, after which CFUs were enumerated. Adhesion was reported as total CFUs divided by the number of bronchial cells in the well as determined by cell counts of a bacteria-free control well of 16HBE14o- cells.

Figure 9:
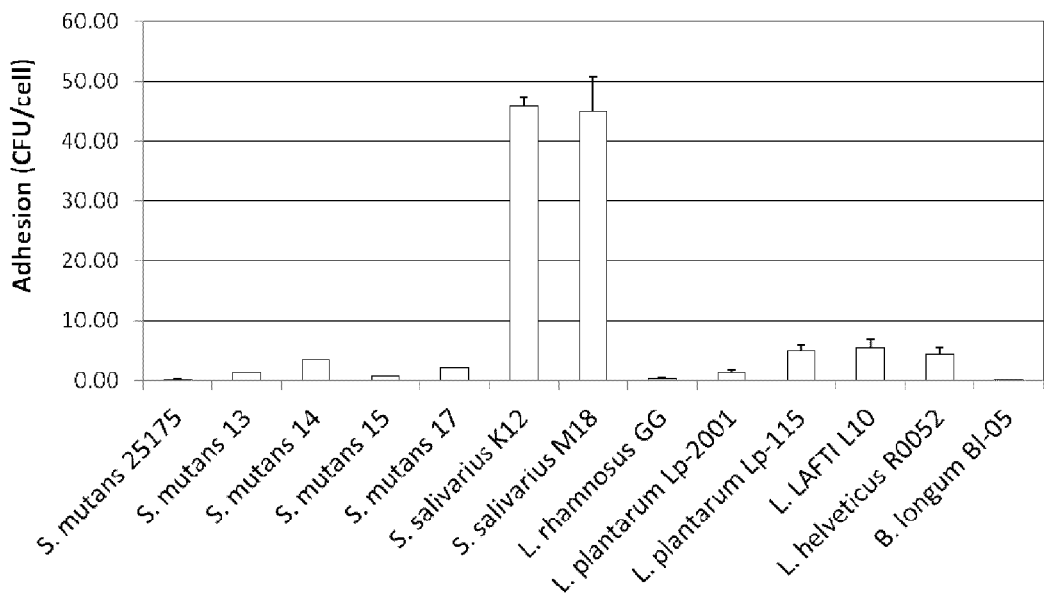
FIG. 9 depicts a graph showing adhesion of various probiotic strains, and strains of *S. mutans* to human bronchial epithelial cell line 16HBE14o-.

To deliver its effects, the bacteria would have to co-localize with the *S. mutans* within the oral cavity. To test the potential of the probiotic bacteria to stay within the oral cavity, binding affinity assays were performed (FIG. 9). The assay tested adherence of the bacteria to a monolayer of 16HBE14o- human bronchial epithelial cells, which share a cell linage with oral epithelial cells and resemble them in phenotype. Bacteria were seeded into MEM media and allowed to grow for 5 hours before the free bacteria were washed away, and CFU counts made of the remaining disrupted eukaryotic and bacterial cell mixture. It was found that in general, the S. mutans pathogens did not adhere well to the cells, and nor did the lactobacilli tested (FIG. 9). The *S. salivarius*, which were originally isolated from the human throat, however adhered very tightly by comparison.

EXAMPLE 5

Co-aggregation with *S. Mutans*

The various probiotic bacteria or *S. mutans* were inoculated into 1 mL of liquid MRS for either lactobacilli or bifidobacteria, or BHYE for streptococci, and then incubated overnight at 37° C. in microaerophilic conditions. The tubes were then centrifuged at 2000 rpm for 5 min and the supernatant aspirated, and then re-suspended in 1 mL PBS. This step was repeated 3 times. The suspended cells were then serially diluted in 100 μL PBS up to 128-fold in 2-fold serial dilution steps in a 96 well plate. The absorbance was read from the plate at 600 nm using an EON microplate reader (BioTek). From the resultant data absorbance versus dilution curves were created, and the dilution for an absorbance of 0.3 was extrapolated for each bacterium tested. Triplicate wells containing 200 μL of suspended bacteria were diluted directly in a 96 well plate according to the extrapolation. For each bacterium 100 μL of the same dilution was also added together with 100 μL of diluted *S. mutans*. The mixtures were uniformly dispersed by pipetting the wells up and down with a multichannel pipette. The plate was then sealed with a sterile clear plastic film, and then immediately incubated in the microplate reader at 37° C. along with a PBS blank. The wells were read at 600 nm after 6 hours.

Figure 10:
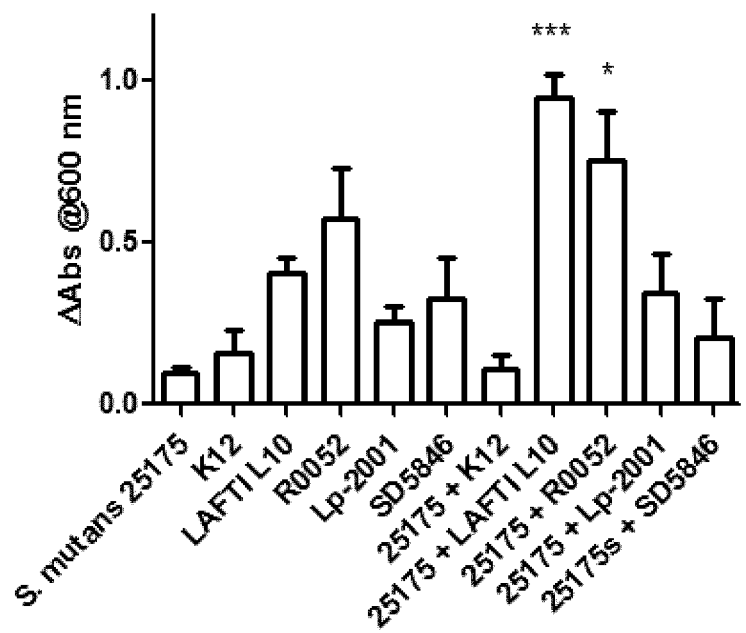
FIG. 10 depicts a graph showing comparison of the aggregation of various probiotic strains with *S. mutans* 25175. Comparison was made by one-way ANOVA with Bonferroni post hoc test (*$p<0.05$, $p<0.01$, *$p<0.001$).

The potential of the strains to adhere and interact directly with the *S. mutans* through an aggregation assay was also assessed (FIG. 10). Individual strains, and also equal part mixtures with *S. mutans* were assayed for absorbance changes at 600 nm when incubated at 37° C. An elevated absorbance indicates faster settling as a result of aggregation, when compared to either strain individually. The experiment shows that *S. mutans* does not auto-aggregate without a biofilm. However the addition of either strain of *L. helveticus* (LAFTI L10 or R0052) led to a significantly increased absorbance compared to either bacterium alone.

EXAMPLE 6

Discussion of In Vitro Effects

It has been here demonstrated that unique properties of particular strains of bacteria have the potential to modify the oral micro-floral environment for the amelioration of oral health and the reduction in dental caries causing *S. mutans*. This conclusion is underpinned by the specific finding that strains of the species *L. helveticus* (LAFTI L10 and R0052) inhibit pathogens *S. mutans* better than all strains tested including *S. salivarius* M18 and *L. rhamnosus* GG, which are well established strains in the treatment of dental caries.

Secondly, there is substantial and significant synergism between the strains *L. plantarum* SD5870 and *L. helveticus* LAFTI L10 in their combined ability to inhibit five strains of freshly isolated *S. mutans* as well as a *S. mutans* strain that is very pathogenic. The co-aggregation of and *L. helveticus* LAFTI L10 with *S. mutans* in vitro further underscores its strong potential to localize and deliver its effects in the oral cavity. Finally, the probiotic combination was shown to have synergistic *S. mutans*-reducing potential when combined together in an in vitro model of dental caries. This finding is unexpected since we had previously observed that the combination of two or more different probiotics normally resulted in poorer inhibition than any one of the probiotics alone. Combinations may generally lead to poorer inhibition because the different probiotics in the combination may compete with each other as well as inhibit each other. Even maintaining inhibition at the same level as compared to a single probiotic is unexpected, let alone finding synergy between combinations of probiotics.

Several bacterial strains have reliably been demonstrated to affect dental caries pathogens through various mechanisms. Notably, *S. salivarius* M18 was shown both in in vitro and in clinical studies to have an anti-*S. mutans* activity. There was also considerable clinical research interest demonstrating the probiotic *Lactobacillus rhamnosus* GG to have anti-dental caries effects in short term and long term studies. In the present invention it was demonstrated that several strains of probiotic bacteria exceeded these probiotics in their *S. mutans* antagonism. While no antagonism of the *S. mutans* strains was observed using *L. rhamnosus* GG, considerable antagonism was observed using *S. salivarius* M18. It is notable however that several strains of probiotic tested including *L. plantarum* SD5870, and *B. longum* SD5846, and the related strain *S. salivarius* K12, were all observed to have greater antagonism than *S. salivarius* M18 for at least one strain of *S. mutans*, while the two *L. helveticus* strains studied (LAFTI L10 and R0052) had in fact greater or equal antagonism for all strains tested.

Of greatest interest is that when the strain *L. helveticus* LAFTI L10 was combined with *L. plantarum* SD5870, strong anti-*S. mutans* synergism was observed for all five pathogens tested. The observed antagonism was stronger for this combination than for any other individual probiotic strain or combination tested, and was at least three times more effective at antagonizing than the two individual probiotics added together, for all five of the *S. mutans* strains.

Although it is unknown what metabolic mechanisms underlay the synergism, it is known that some strains of *L. helveticus* secrete bacteriocins like helveticin J, and helveticin V-1829, and likewise strains of *L. plantarum* have a variety of bacteriocins and other antimicrobial substances coded at the pln locus, whose secretion is regulated through a quorum mechanism. Though it is unknown whether *L. plantarum* SD5870 expresses any antimicrobial factors, their expression though variable is thought to be relatively common among *L. plantarum* strains. Antimicrobial peptides that antagonize *S. mutans* may be particularly effective in combinations of complementary lethality when secreted by the two probiotics.

It is interesting that the 4 non-streptococci strains that had *S. mutans* antagonism were all among the strongest $H_2O_2$ producers. While *S. salivarius* K12 and M18 may exert anti-*S. mutans* activity through secretion of specific bacteriocins, it appears likely that *L. plantarum* SD5870 and *Lactobacillus helveticus* LAFTI L10 do so at least partially through the secretion of $H_2O_2$. *S. mutans* is reported as being able to both produce and degrade hydrogen peroxide, but is nevertheless also readily susceptible to it, presumably at threshold concentrations. Levels of hydrogen peroxide localized around *S. mutans* in vivo, may be further increased by the direct aggregation that was observed of *L. helveticus* LAFTI L10 with *S. mutans*, and thereby act as an additional factor by which a high degree of antagonism is achieved.

The findings here support the conclusion that *L. helveticus* has significant antagonism against *S. mutans*, and further that the specific combination of *L. helveticus* LAFTI L10 and *L. plantarum* SD5870 act synergistically to antagonize and inhibit the growth of *S. mutans* in an in vitro model of oral health. These findings have significant implications for microbiological-based treatment strategies of dental caries.

EXAMPLE 7

In-vivo Effects

In-vivo effects may be determined as follows. A randomized, double blinded, placebo controlled clinical trial is conducted with 30-40 subjects per group. Subjects are treated with equal doses of a minimum of 1 billion CFU *L. helveticus* LAFTI 110 and *L. plantarum* SD5870 twice daily in a probiotic lozenge following brushing for a period of 28-30 days. A decrease in the detection of precarious demineralised surface area of >20% may be expected as determined using highly sensitive frequency-domain infrared photothermal radiometry and modulated luminescence. A decrease in *S. mutans* and plaque levels is also expected.

It is anticipated that the addition of casein phosphate peptide-amorphous calcium phosphate (CPP-ACP) or other remineralization agent will demonstrate significant in vivo effects as follows. A randomized, double blinded, placebo controlled clinical trial is conducted with 30-40 subjects per group. The study would comprise 4 arms as follows: a first treatment group where subjects are treated with equal doses of a minimum of 1 billion CFU *L. helveticus* LAFTI 110 and *L plantarum* SD5870; a second treatment group where subjects are treated with a combination of 1 billion CFU *L. helveticus* LAFTI 110 and *L plantarum* SD5870 and an effective dose of CPP-ACP or other remineralization agent; a third treatment group where subjects are treated with an effective dose of CPP-ACP or other remineralization agent; and a fourth treatment group where subjects are treated with a placebo control. The study would continue with twice daily doses in probiotic lozenges following brushing for a period of 28-30 days. A decrease in the detection of precarious demineralised surface area of >20% may be expected as determined using highly sensitive frequency-domain infrared photothermal radiometry and modulated luminescence. A decrease in *S. mutans* and plaque levels is also expected.

EXAMPLE 8

Lozenge Formulation and Stability $7/16$-inch round lozenges are formulated in accordance with Table 2.

TABLE 2

| Ingredient | Amount per Lozenge (mg) |
| --- | --- |
| *Lactobacillus helveticus* LAFTI L10 | 45 |
| *Lactobacillus plantarum* Lp-2001 (SD-5870) | 25 |
| *S. salivarius* M18 (BAA-2593) | 6 |
| Recaldent ™ (CPP-ACP) | 20 |
| Isomalt | 160 |
| Fructose | 100 |
| Microcrystalline Cellulose | 70 |
| Dextrose | 50 |
| Stearic Acid | 15 |
| Dicalcium Phosphate | 10 |
| Citric Acid | 6 |
| Cherry Pomegranate Flavor (natural) | 3 |
| Total | 510 |

Sealed packages of the lozenges are stored at room temperature (20-25° C.) at an ambient humidity of 60-65%. Bacteria are cultured from the lozenges at defined time points according to an industry standard selective spread plate method. Thus, lozenges are dissolved in phosphate buffered saline (PBS), serially diluted, and plated onto selective agar for *S. salivarius* (CABK12) and *Lactobacilli* (Rogosa) agar plates in triplicate. CFU counts are made following 48 hour incubation at 37° C. in microaerophilic conditions. Even after 27 months, there are still substantial live probiotic strains with at least about $4 \times 10^8$ CFU/lozenge. There are substantial and adequate numbers of live bacteria to deliver probiotics health benefits.

EXAMPLE 9

Deferred Antagonism in Prior Art Products

Commercially available probiotic products were tested with the deferred antagonism assay described above. Table 3 provides the probiotic bacterial composition for each product.

TABLE 3

| Product | Probiotic bacteria | Tested CFU/lozenge |
| --- | --- | --- |
| A | *S. salivarius* K12 and M18 | $3.97 \times 10^5$ |
| B | *Lactobacillus rhamnosus, L. plantarum, L. reuteri, L. paracasei, L. salivarius, S. salivarius* K12 | $9.72 \times 10^8$ |
| C | *Streptococcus uberis* KJ2, *S. oralis* KJ3, *S. rattus* JH145 | $2.2 \times 10^9$ |
| D | *L. reuteri* DSM 17938 (*L reuteri* Protectis ™) | $9.17 \times 10^6$ |
| E | *L. reuteri* DSM 17938, *L. reuteri* PTA 5289 | $3.67 \times 10^7$ |

In brief, one lozenge of each product was dissolved in 5 mL of 1× PBS by shaking for 2 h at 37° C. in sterile conditions. Then, with the help of a cotton swab, the dissolution was spread within a 1 cm wide streak across the diameter of BHI and BHI supplemented with $CaCO_3$ agar plates. These plates were incubated for 48 h at 37° C. in microaerophilic conditions, then the grown bacteria were removed and the agar was sterilized. After, 5 different strains of *S. mutans* (ATCC strain and Integra's isolates 13, 14, 15 and 17) were swabbed across the plates, perpendicularly to the probiotic streak and left to grow for another 48 h. This procedure was repeated twice, each of them using triplicates for each condition. Unlike compositions of the present invention, no growth inhibition was observed for any of the six replicates of each condition for any of the commercially available probiotic products tested.

It should also be noted that the probiotic bacterial count of about $4 \times 10^8$ CFU/lozenge after 27 months of storage of a lozenge of the present invention as described in Example 8 compares very favorably with the prior art products that were tested, and is considerably better than over half of the prior art products tested.

REFERENCES

The contents of the entirety of each of which are incorporated by this reference.

Burton J P, et al. (2013) The influence of the probiotic *Streptococcus salivarius* M18 on indices of dental health in children: a randomised double-blind placebo-controlled trial. *Journal of medical microbiology*. doi: 10.1099/jmm.0.056663-0.

Caglar E, Kargul B, Tanboga I. (2005a) Bacteriotherapy and probiotics' role on oral health. *Oral diseases*. 11, 131-7.

Caglar E, et al. (2005b) Effect of yogurt with *Bifidobacterium* DN-173 010 on salivary mutans streptococci and lactobacilli in young adults. *Acta odontologica Scandinavica*. 63, 317-20.

Caglar E, Cildir S K, Ergeneli S, Sandalli N, Twetman S. (2006) Salivary mutans streptococci and lactobacilli levels after ingestion of the probiotic bacterium *Lactobacillus reuteri* ATCC 55730 by straws or tablets. *Acta odontologica Scandinavica*. 64, 314-8.

Caglar E, et al. (2008) Short-term effect of ice-cream containing *Bifidobacterium lactis* Bb-12 on the number of salivary mutans streptococci and lactobacilli. *Acta odontologica Scandinavica*. 66, 154-8.

Kang M-S, et al. (2011) Inhibitory effect of *Lactobacillus reuteri* on periodontopathic and cariogenic bacteria. *Journal of microbiology* (Seoul, Korea). 49, 193-9.

Keller M K, Hasslöf P, Stecksén-Blicks C, Twetman S. (2011) Co-aggregation and growth inhibition of probiotic lactobacilli and clinical isolates of mutans streptococci: an in vitro study. *Acta odontologica Scandinavica*. 69, 263-8.

Näse L. et al. (2001) Effect of long-term consumption of a probiotic bacterium, *Lactobacillus rhamnosus* GG, in milk on dental caries and caries risk in children. *Caries research*. 35, 412-20.

Oho T, Yamashita Y, Shimazak, Y, Kushiyama M, Koga T. (2000) Simple and rapid detection of *Streptococcus mutans* and *Streptococcus sobrinus* in human saliva by polymerase chain reaction. *Oral microbiology and immunology*. 15, 258-62.

Saha S, Tomaro-Duchesneau C, Tabrizian M, Prakash S. (2012) Probiotics as oral health biotherapeutics. *Expert opinion on biological therapy*. 12, 1207-20.

Stecksén-Blicks C, Sjöstrom I, Twetman S. (2009) Effect of long-term consumption of milk supplemented with probiotic lactobacilli and fluoride on dental caries and general health in preschool children: a cluster-randomized study. *Caries research*. 43, 374-81.

Tagg J R, Bannister L V. (1979) "Fingerprinting" beta-haemolytic streptococci by their production of and sensitivity to bacteriocine-like inhibitors. *Journal of medical microbiology*. 12, 397-411.

Tagg J R, Dierksen K P. (2003) Bacterial replacement therapy: adapting "germ warfare" to infection prevention. *Trends in biotechnology*. 21, 217-23.

Taipale T, Pienihäkkinen K, Salminen S, Jokela J, Söderling E. (2012) *Bifidobacterium animalis* subsp. lactis BB-12 administration in early childhood: a randomized clinical trial of effects on oral colonization by mutans streptococci and the probiotic. *Caries research*. 46, 69-77.

Wang J. et al. (2012) Synergistic effects of nanosecond pulsed electric fields combined with low concentration of gemcitabine on human oral squamous cell carcinoma in vitro. *PloS one*. 7, e43213.

The novel features of the present invention will become apparent to those of skill in the art upon examination of the detailed description of the invention. It should be understood, however, that the scope of the claims should not be limited by the preferred embodiments set forth in the examples, but should be given the broadest interpretation consistent with the specification as a whole.

The invention claimed is:

1. A method of treating an oral condition or disease in a subject, the method comprising orally administering a composition comprising an effective amount of a probiotic used for treating or preventing an oral condition or disease in a subject, the probiotic comprises a *Lactobacillus helveticus* strain wherein the oral condition or disease is selected from dental caries, halitosis, gingivitis, mouth ulcers, aphthous stomatitis, candidiasis, and combinations thereof, wherein the *Lactobacillus helveticus* strain is selected from *Lactobacillus helveticus* LAFTI L10, *Lactobacillus helveticus* R0052, or a mixture thereof.

2. The method of claim 1, wherein the *Lactobacillus helveticus* strain is *Lactobacillus helveticus* LAFTI L10.

3. The method of claim 1, wherein the probiotic further comprises a *Lactobacillus plantarum* strain.

4. The method of claim 3, wherein the *Lactobacillus plantarum* strain comprises *Lactobacillus plantarum* SD5870.

5. The method of claim 1, wherein the probiotic further comprises one or more bifidobacteria.

6. The method of claim 5, wherein the bifidobacteria comprises *Bifidobacterium longum* SD5846.

7. The method of claim 1, wherein the composition further comprises a remineralization agent.

8. The method of claim 7, wherein the remineralization agent comprises casein phosphate peptide-amorphous calcium phosphate.

9. The method of claim 1, wherein the oral condition or disease is dental caries.

* * * * *